United States Patent
Gloss et al.

(10) Patent No.: US 8,795,353 B2
(45) Date of Patent: Aug. 5, 2014

(54) HOLDER DEVICES FOR ANNULOPLASTY DEVICES HAVING A PLURALITY OF ANTERIOR-POSTERIOR RATIOS

(75) Inventors: Michael A. Gloss, Minneapolis, MN (US); Stephen Kuehn, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 986 days.

(21) Appl. No.: 12/358,940

(22) Filed: Jan. 23, 2009

(65) Prior Publication Data

US 2009/0192606 A1 Jul. 30, 2009

Related U.S. Application Data

(60) Provisional application No. 61/062,412, filed on Jan. 25, 2008.

(51) Int. Cl.
*A61F 2/24* (2006.01)

(52) U.S. Cl.
USPC .......................................................... 623/2.11

(58) Field of Classification Search
USPC ...................................... 623/2.36, 2.37, 2.11
See application file for complete search history.

(56) References Cited

U.S. PATENT DOCUMENTS

| | | |
|---|---|---|
| 3,656,185 A | 4/1972 | Carpentier |
| 3,966,401 A | 6/1976 | Hancock et al. |
| 4,050,893 A | 9/1977 | Hancock et al. |
| 4,055,861 A | 11/1977 | Carpentier et al. |
| 4,164,046 A | 8/1979 | Cooley |
| 4,182,446 A | 1/1980 | Penny |
| 4,917,698 A | 4/1990 | Carpentier et al. |
| 5,011,481 A | 4/1991 | Myers et al. |
| 5,041,130 A | 8/1991 | Cosgrove et al. |
| 5,061,277 A | 10/1991 | Carpentier et al. |
| 5,104,407 A | 4/1992 | Lam et al. |
| 5,201,880 A | 4/1993 | Wright et al. |
| 5,258,021 A | 11/1993 | Duran |
| 5,290,300 A | 3/1994 | Cosgrove et al. |
| 5,306,296 A | 4/1994 | Wright et al. |
| 5,350,420 A | 9/1994 | Cosgrove et al. |
| 5,376,112 A | 12/1994 | Duran |
| 5,476,510 A * | 12/1995 | Eberhardt et al. ............ 623/2.11 |

(Continued)

FOREIGN PATENT DOCUMENTS

| | | |
|---|---|---|
| EP | 0 257 874 | 3/1988 |
| EP | 0 338 994 | 10/1989 |

(Continued)

OTHER PUBLICATIONS

Ahmadi, A., et al., "Hemodynamic Changes Following Experimental Production and Correction of Acute Mitral Regurgitation With an Adjustable Ring Prosthesis," The Thoracic and Cardiovascular Surgeon, vol. 36, No. 6, pp. 313-319 (1988).

(Continued)

*Primary Examiner* — Tuan V Nguyen (57) ABSTRACT

An adjustable annuloplasty device holder has a member having an anterior segment and a posterior segment that are shaped to hold an anterior portion and a posterior portion, respectively, of an annuloplasty device. The anterior segment has a given size and the posterior segment is adjustable in order to change the anterior-posterior ratio of the holder to accommodate annuloplasty devices having a plurality of different anterior-posterior ratios.

9 Claims, 2 Drawing Sheets

(56) References Cited

U.S. PATENT DOCUMENTS

| | | | |
|---|---|---|---|
| 5,496,336 A | 3/1996 | Cosgrove et al. | |
| 5,522,884 A | 6/1996 | Wright | |
| 5,593,424 A | 1/1997 | Northrup, III | |
| 5,601,576 A | 2/1997 | Garrison | |
| 5,607,471 A | 3/1997 | Seguin et al. | |
| 5,669,919 A | 9/1997 | Sanders et al. | |
| 5,674,279 A | 10/1997 | Wright et al. | |
| 5,674,280 A | 10/1997 | Davidson et al. | |
| 5,683,402 A | 11/1997 | Cosgrove et al. | |
| 5,716,397 A | 2/1998 | Myers | |
| 5,824,066 A | 10/1998 | Gross | |
| 5,860,992 A | 1/1999 | Daniel et al. | |
| 5,972,030 A | 10/1999 | Garrison et al. | |
| 6,102,945 A | 8/2000 | Campbell | |
| 6,143,024 A | 11/2000 | Campbell | |
| 6,159,240 A | 12/2000 | Sparer et al. | |
| 6,165,183 A | 12/2000 | Kuehn et al. | |
| 6,174,332 B1 | 1/2001 | Loch et al. | |
| 6,183,512 B1 | 2/2001 | Howanec, Jr. et al. | |
| 6,187,040 B1 | 2/2001 | Wright | |
| 6,217,610 B1 | 4/2001 | Carpentier et al. | |
| 6,231,602 B1 | 5/2001 | Carpentier et al. | |
| 6,283,993 B1 | 9/2001 | Cosgrove et al. | |
| 6,319,280 B1 | 11/2001 | Schoon | |
| 6,368,348 B1 | 4/2002 | Gabbay | |
| 6,406,492 B1 | 6/2002 | Lytle | |
| 6,416,548 B2 | 7/2002 | Chinn et al. | |
| 6,416,549 B1 | 7/2002 | Chinn et al. | |
| 6,528,107 B2 | 3/2003 | Chinn et al. | |
| 6,565,603 B2 | 5/2003 | Cox | |
| 6,602,289 B1 | 8/2003 | Colvin et al. | |
| 6,695,866 B1 | 2/2004 | Kuehn et al. | |
| 6,726,717 B2 | 4/2004 | Alfieri et al. | |
| 6,749,630 B2 | 6/2004 | McCarthy et al. | |
| 6,786,924 B2 | 9/2004 | Ryan et al. | |
| 6,797,002 B2 | 9/2004 | Spence et al. | |
| 6,805,710 B2 | 10/2004 | Bolling et al. | |
| 6,858,039 B2 | 2/2005 | McCarthy | |
| 6,908,482 B2 | 6/2005 | McCarthy et al. | |
| 6,955,689 B2 | 10/2005 | Ryan et al. | |
| 7,294,148 B2 | 11/2007 | McCarthy | |
| 7,329,280 B2 | 2/2008 | Bolling et al. | |
| 7,367,991 B2 | 5/2008 | McCarthy et al. | |
| 7,371,259 B2 | 5/2008 | Ryan et al. | |
| 7,377,940 B2 | 5/2008 | Ryan et al. | |
| 7,575,595 B2 | 8/2009 | Ingle et al. | |
| 7,608,103 B2 | 10/2009 | McCarthy | |
| 7,674,286 B2 | 3/2010 | Alfieri et al. | |
| 7,993,395 B2* | 8/2011 | Vanermen et al. | 623/2.36 |
| 2001/0010018 A1 | 7/2001 | Cosgrove et al. | |
| 2001/0021874 A1 | 9/2001 | Carpentier et al. | |
| 2001/0034551 A1 | 10/2001 | Cox | |
| 2001/0041933 A1 | 11/2001 | Thoma | |
| 2001/0049557 A1 | 12/2001 | Chinn et al. | |
| 2001/0049558 A1 | 12/2001 | Liddicoat et al. | |
| 2002/0129820 A1 | 9/2002 | Ryan et al. | |
| 2002/0169503 A1 | 11/2002 | Lytle | |
| 2002/0173844 A1 | 11/2002 | Alfieri et al. | |
| 2003/0045929 A1 | 3/2003 | McCarthy et al. | |
| 2003/0093148 A1 | 5/2003 | Bolling et al. | |
| 2003/0125715 A1 | 7/2003 | Kuehn et al. | |
| 2004/0006384 A1 | 1/2004 | McCarthy | |
| 2004/0034410 A1* | 2/2004 | Holmberg | 623/2.11 |
| 2004/0088047 A1 | 5/2004 | Spence et al. | |
| 2005/0004665 A1 | 1/2005 | Aklog | |
| 2005/0049698 A1 | 3/2005 | Bolling et al. | |
| 2005/0131533 A1 | 6/2005 | Alfieri et al. | |
| 2005/0182487 A1 | 8/2005 | McCarthy et al. | |
| 2005/0256567 A1 | 11/2005 | Lim et al. | |
| 2005/0256568 A1 | 11/2005 | Lim et al. | |
| 2005/0256569 A1 | 11/2005 | Lim et al. | |
| 2005/0267572 A1 | 12/2005 | Schoon et al. | |
| 2006/0025856 A1 | 2/2006 | Ryan et al. | |
| 2006/0074486 A1* | 4/2006 | Liddicoat et al. | 623/2.36 |
| 2006/0129236 A1 | 6/2006 | McCarthy | |
| 2007/0100441 A1 | 5/2007 | Kron et al. | |
| 2007/0156234 A1 | 7/2007 | Adzich et al. | |
| 2008/0058924 A1 | 3/2008 | Ingle et al. | |
| 2008/0071367 A1* | 3/2008 | Bergin et al. | 623/2.11 |
| 2009/0157176 A1 | 6/2009 | Carpentier et al. | |
| 2009/0177276 A1 | 7/2009 | Carpentier et al. | |
| 2009/0192605 A1 | 7/2009 | Gloss et al. | |
| 2009/0264996 A1 | 10/2009 | Vanermen et al. | |
| 2009/0287303 A1 | 11/2009 | Carpentier | |

FOREIGN PATENT DOCUMENTS

| | | |
|---|---|---|
| EP | 0 495 417 | 7/1992 |
| EP | 1 034 753 | 2/2005 |
| WO | 91/17721 | 11/1991 |
| WO | 99/04730 | 2/1999 |
| WO | 99/29269 | 6/1999 |
| WO | 99/49816 | 10/1999 |
| WO | 00/23007 | 4/2000 |
| WO | 00/59408 | 10/2000 |
| WO | 00/62715 | 10/2000 |
| WO | 00/74603 | 12/2000 |
| WO | 02/074197 | 9/2002 |
| WO | 03/020178 | 3/2003 |
| WO | 03/053289 | 7/2003 |
| WO | 2007/143077 | 12/2007 |

OTHER PUBLICATIONS

Alonso-Lei, "Adjustable Annuloplasty for Tricuspid Insufficiency," The Annals of Thoracic Surgery, (1988) 46(3), pp. 368-369.

Alonso-Lej, F., "The 'dynamic' mitral ring: A new concept in treating mitral insufficiency," Recent Progress in Mitral Valve Disease, pp. 45 and 443-449 (1984).

AnnuloFlex® and AnnuloFlo® Systems, Implantation techniques for mitral and tricuspid indications, CarboMedics (2003) (24 pages).

Belcher, J.R., "The Surgical Treatment of Mitral Regurgitation," British Heart Journal, vol. 26, pp. 513-523 (1964).

Bex J.P. and Lecompte Y., "Tricuspid valve repair using a flexible linear reducer," J. Cardiac Surg., 1:151 (1986).

Bolling, "Mitral Valve Reconstruction in the Patient with Heart Failure," Heart Failure Reviews, (2001) 6, pp. 177-185.

Bolling, et al., "Surgical Alternatives for Heart Failure," The Journal of Heart and Lung Transplantation, (2001) 20(7), pp. 729-33.

Bolling, S.F., et al., "Surgery for Acquired Heart Disease," The Journal of Thoracic and Cardiovascular Surgery, vol. 109, No. 4, pp. 676-683 (1995).

Bolling, S.F., "Mitral Reconstruction in Cardiomyopathy," The Journal of Heart Valve Disease, vol. 11, Suppl. 1, pp. S26-S31 (2002).

Carpentier-Edwards® Annuloplasty Rings (3 pages) (copy can be found in the file history for U.S. Appl. No. 10/918,503).

Carpentier-Edwards Physio™ Annuloplasty Ring (3 pages) (copy can be found in the file history for U.S. Appl. No. 10/918,503).

Carpentier, A., "La Valvuloplastie Reconstitutive: Une Nouvelle Technique de Valvuloplastie Mitrale," Technique Chirugicale, No. 7, pp. 251-255 (1969).

Carpentier, A., et al., "A New Reconstructive Operation for Correction of Mitral and Tricuspid Insufficiency," The Journal of Thoracic and Cardiovascular Surgery, vol. 61, No. 1, pp. 1-13 (1971).

Carpentier A., Deloche A., Hanania G., et al., "Surgical management of acquired tricuspid valve disease," J. Thorac. Cardiovasc. Surg., 67:53 (1974).

Carpentier, A.F., et al., "The 'Physio-Ring': An Advanced Concept in Mitral Valve Annuloplasty," Ann. Thorac. Surg., vol. 60, No. 5, pp. 1177-1186 (1995).

Castells, E., et al., "Long-Term Results with the Puig Massana-Shiley Annuloplasty Ring," The Journal of Cardiovascular Surgery, Abstracts, vol. 24, No. 4, p. 387 (1983).

Chachques, J.C., et al., "Absorbable Rings for Pediatric Valvuloplasty: Preliminary Study," Supplement IV to Circulation, vol. 82, No. 5, pp. IV-82-IV-88 (1990).

Cochran, et al., "Effect of Papillary Muscle Position on Mitral Valve Function: Relationship to Homografts," Ann. Thorac. Surg, (1998) 66:SS155-61.

(56) References Cited

OTHER PUBLICATIONS

Cooley, D.A., et al., "Mitral Leaflet Prolapse: Surgical Treatment using a Posterior Annular Collar Prosthesis," Cardiovascular Diseases Bulletin of the Texas Heart Institute, vol. 3, No. 4, pp. 438-443 (1976).

Cooley, D.A., "Ischemic Mitral Insufficiency," Cardiac Surgery: State of the Art Reviews, vol. 6, No. 2, pp. 237-249 (1992).

Cooley, D.A., et al., "A Cost-Effective Dacron Annuloplasty Ring," The Annals of Thoracic Surgery, vol. 56, pp. 185-186 (1993).

Cosgrove, D.M., III, et al., "Initial Experience with the Cosgrove-Edwards Annuloplasty System," The Annals of Thoracic Surgery, vol. 60, pp. 499-504 (1995).

Dagum et al., "Three-dimensional geometric comparison of partial and complete flexible mitral annuloplasty rings," The J. of Thorac. and Cardiovasc. Surg., vol. 122, No. 4 (2001).

Deloche, A., et al., "Valve Repair with Carpentier Techniques," The Journal of thoracic and Cardiovascular Surgery, vol. 99, No. 6, pp. 990-1002 (1990).

Department of Health & Human Services letter and attachments regarding file K926138, Carpentier-Edwards Physio™ Annuloplasty Ring, Model 4450 Mitral, dated Jun. 22, 1993 (295 pages).

Duran, C.,M.G., et al., "Valve Repair in Rheumatic Mitral Disease," Supplement to Circulation, vol. 84, No. 5, pp. III 125-III 132 (1990).

Duran, C.G., et al., "Clinical and Hemodynamic Performance of a Totally Flexible Prosthetic Ring for Atrioventricular Valve Reconstruction," The Annals of Thoracic Surgery, vol. 22, No. 5, pp. 458-463 (1976).

Duran, C.G., "Reconstructive procedures of the Mitral Valve Including Ring Annuloplasty," Modern Technics in Surgery, 20 (1979).

Durán, C.M.G., et al., "A New Absorbable Annuloplasty Ring in the Tricuspid Position: An Experimental Study," The Thoracic and Cardiovascular Surgeon, vol. 34, No. 6, pp. 377-379 (1986).

Duran, C.G., et al., "Stability of Mitral Reconstructive Surgery at 10-12 Years for Predominantly Rheumatic Valvular Disease," Circulation Supplement I, vol. 78, No. 3, pp. 1-91-1-96 (1988).

Erk, M.K., et al., "Semi-frame Mitral Annuloplasty," Cardiac Reconstructions pp. 157-163 (1989).

Erk, M.K., "Morphological and Functional Reconstruction of the Mitral Valve: A New Annuloplastic Procedure," Texas Heart Institute Journal, vol. 9, pp. 329-334 (1982).

Flachskampf, et al., "Analysis of Shape and Motion of the Mitral Annulus in Subjects With and Without Cardiomyopathy by Echocardiographic 3-Dimensional Reconstruction," Journal of the American Society of Echocardiography, (2000) 13(4), pp. 277-287.

Freed, et al., "Prevalence and Clinical Outcome of Mitral-Valve Prolapse," The New England Journal of Medicine, (1999) 341(1), pp. 1-7.

Fundarò, P., et al., "Polytetrafluoroethylene Posterior Annuloplasty for Mitral Regurgitation," The Annals of Thoracic Surgery, Correspondence, vol. 50, No. 1, pp. 165-166 (1990).

Galler M. Kronzon I, Slater J., et al., "Long-term follow-up after mitral valve reconstruction: incidence of post-operative left ventricular out flow obstruction," Circulation, 74:I-99 (1986).

Gatti, et al., "Preliminary experience in mitral valve repair using the Cosgrove-Edwards annuloplasty ring," Interact Cardiovasc Thorac Surg, (2003) 2:256-261.

Ghosh, P.K., "Mitral Annuloplasty: A Right-Side View," The Journal of Heart Valve Disease, vol. 5, pp. 286-293 (1996).

Gorman, et al., "Dynamic Three-Dimensional Imaging of the Mitral Valve and Left Ventricle by Rapid Sonomicrometry Array Localization," J Thorac Card Surg, 112(3), (1996) pp. 712-726.

Gorman, et al., "The Effect of Regional Ischemia on Mitral Valve Annular Saddle Shape," Ann Thorac Surg (2004) 77, pp. 544-548.

Gorton, M.E., et al., "Mitral Valve Repair Using a Flexible and Adjustable Annuloplasty Ring," The Annals of Thoracic Surgery, vol. 55, pp. 860-863 (1993).

Gregori, F., et al., "Mitral Valvuloplasty with a New Prosthetic Ring," Official Journal of the European Association for Cardio-thoracic Surgery, vol. 8, No. 4, pp. 168-172 (1994).

Gregori, F., Jr., et al., "Um Novo Modelo De Anel Protetico Para Pacientes Com Insuficiencia Valvar Mitral. Relato de Dois Casos," Arquivos Brasileiros de Cardiologia, vol. 50, No. 6, pp. 417-420 (1988).

Haverich, et al., "Experimental and Clinical Experiences with Double-velour Woven Dacron Prostheses," Thorac. Cardiovasc. Surgeon 34 (1986) pp. 52-53.

Hendren, W.G., et al., "Mitral Valve Repair for Ischemic Mitral Insufficiency," The Annals of Thoracic Surgery, vol. 52, pp. 1246-1252 (1991).

Henze, A., et al., "The Adjustable Half-Moon: An Alternative Device for Tricuspid Valve Annuloplasty," Scandinavian Journal of Thoracic and Cardiovascular Surgery, vol. 18, pp. 29-32 (1984).

Jimenez, et al., "Effects of a Saddle Shaped Annulus on Mitral Valve Function and Chordal Force Distribution: An In Vitro Study," Annals of Biomedical Engineering, (2003) vol. 31, pp. 1171-1181.

Kasegawa, H., et al., "Physiologic Remodeling Annuloplasty to Retain the Shape of the Anterior Leaflet: A New Concept in Mitral Valve Repair," The Journal of Heart Valve Disease, vol. 6, pp. 604-607 (1997).

Katz, N.M., "Current Surgical Treatment of Valvular Heart Disease," American Family Physician, vol. 52, No. 2, pp. 559-568 (1995).

Kaye, D.M., et al., "Feasibility and Short-Term Efficacy of Percutaneous Mitral Annular Reduction for the Therapy of Heart Failure—Induced Mitral Regurgitation," Circulation, Brief Rapid Communication, No. 108, pp. 1795-1797 (2003).

Kurosawa, H., et al., "Mitral Valve Repair by Carpentier-Edwards Physio Annuloplasty Ring," the Japanese Journal of Thoracic and Cardiovascular Surgery, vol. 47, pp. 355-360 (1999).

Lachmann, J., M.D., et al., "Mitral Ring Annuloplasty: An Incomplete Correction of Functional Mitral Regurgitation Associated with Left Ventricular Remodeling," Current Cardiology Reports, vol. 3, pp. 241-246 (2001).

Levine, R.A., et al., "The Relationship of Mitral Annular Shape to the Diagnosis of Mitral Valve Prolapse," Circulation, vol. 75, No. 4, pp. 756-767 (1987).

Levin, et al., "Three-Dimensional Echocardiographic Reconstruction of the Mitral Valve, With Implications for the Diagnosis of Mitral Valve Prolapse," Circulation, 1989; 80(3):589-598.

Martin, S.L., et al., "Echocardiographic Evaluation of Annuloplasty Rings: Comparison of Continuity Equation and Pressure Half-Time Methods," Journal of The American Society of Echocardiography, vol. 5, No. 3, p. 322 (1992).

Medtronic® Sculptor™ Annuloplasty Ring brochure, Medtronic Inc. (1993) (6 pages).

Melo, et al., "Atrioventricular Valve Repair Using Externally Adjustable Flexible Rings," The Journal of Thoracic and Cardiovascular Surgery, (1995) 110(5), pp. 1333-1337.

Miller, "Ischemic mitral regurgitation redux—To repair or to replace?" The Journal of Thoracic and Cardiovascular Surgery, (2001) 122(6), pp. 1059-1062.

Morse, D., et al., "Cardiac Valve Identification Atlas and Guide," Chapter 10 in Guide to Prosthetic Cardiac Valves, edited by Dryden Morse, Robert M. Steiner, and Javier Fernandez, Springer-Verlag New York Inc. (1985).

Murphy, J.P., et al., "The Puig-Massana-Shiley Annuloplasty Ring for Mitral Valve Repair: Experience in 126 Patients," The Annals of Thoracic Surgery, vol. 43, pp. 52-58 (1987).

Ogus, T.N., et al., "Posterior Mitral Annuloplasty with an Adjustable Homemade Ring," Journal of Cardiac Surgery, vol. 17, No. 3, pp. 226-228 (2002).

Pellegrini, A., et al., "Posterior Annuloplasty in the Surgical Treatment of Mitral Insufficiency," The Journal of Heart Valve Disease, vol. 2, pp. 633-638 (1993).

Reece, I.J., et al., "Surgical Treatment of Mitral Systolic Click Syndrome: Results in 37 Patients," The Annals of Thoracic Surgery, vol. 39, No. 2, pp. 155-158 (1985).

Rubenstein, F., et al., "Alternatives in Selection of Rings for Mitral Annuloplasty," Current Opinion in Cardiology, vol. 16, No. 2, pp. 136-139 (2001).

Salati, M., et al., "Annular Remodeling with Pericardial Reinforcement: Surgical Technique and Early Results," The Journal of Heart Valve Disease, vol. 2, pp. 639-641 (1993).

(56) References Cited

OTHER PUBLICATIONS

Salati, M., et al., "Posterior Pericardial Annuloplasty: A Physiocological Correction?", European Journal of Cardio-Thoracic Surgery, vol. 5, pp. 226-229 (1991).

Salgo, et al., "Effect of Annular Shape on Leaflet Curvature in Reducing Mitral Leaflet Street," Circulation, 2002; 106:711-717.

Salvador, L., et al., "The Pericardium Reinforced Suture Annuloplasty: Another Tool Available for Mitral Annulus Repair," Journal of Cardiac Surgery, vol. 8, pp. 79-84 (1993).

Sato, et al., "The Biologic Fate of Dacron Double Velour Vascular Prostheses—A Clinicopathological Study," Japanese Journal of Surgery, (1989) 19(3), pp. 301-311.

Seguin, et al., "Advance in Mitral Valve Repair Using a Device Flexible in Three Dimensions," ASAIO Journal (1996), 42:M368-M371.

Shumway, S.J., et al., "A 'Designer' Annuloplasty Ring for Patients with Massive Mitral Annular Dilation," The Annals of Thoracic Surgery, vol. 46, No. 6, pp. 695-696 (1988).

Smolens, I., et al., "Current Status of Mitral Valve Reconstruction in Patients with Dilated Cardiomyopathy," Ital. Heart J., vol. 1, No. 8, pp. 517-520 (2000).

Smolens, et al., "Mitral valve repair in heart failure," The European Journal of Heart Failure, (2000) 365-371.

Tsakiris, A.G., "The psysiology of the mitral valve annulus," in The Mitral Valve-apluridisciplinary Approach, ed Kalmanson D. Publishing Sciences Group, Acton, Mass., p. 21 (1976).

Victor, S., et al., "Truly Flexible D-Shaped Autogenous Pericardial Ring for Mitral Annuloplasty," The Annals of Thoracic Surgery, vol. 56, pp. 179-180 (1993).

Vongpatanasin, W., et al., "Prosthetic Heart Valves," The New England Journal of Medicine, vol. 335, No. 6, pp. 407-416 (1996).

\* cited by examiner

HOLDER DEVICES FOR ANNULOPLASTY DEVICES HAVING A PLURALITY OF ANTERIOR-POSTERIOR RATIOS

PRIORITY

The present non-provisional patent application claims benefit from U.S. Provisional Patent Application having Ser. No. 61/062,412, filed on Jan. 25, 2008, by Ryan et al., and titled SYSTEM OF ANNULOPLASTY DEVICES WITH VARYING ANTERIOR-POSTERIOR RATIOS AND RELATED DEVICES AND METHODS, wherein the entirety of said provisional patent application is incorporated herein by reference.

TECHNICAL FIELD

The present invention relates generally to devices and methods for repair of heart valves, and more particularly to a holder devices for holding annuloplasty devices having varying anterior-posterior ratios to treat different pathologies.

BACKGROUND OF THE INVENTION

Heart valve disease is a widespread condition in which one or more of the valves of the heart fails to function properly. Various surgical techniques may be used to replace or repair a diseased or damaged valve. In just one way, in a valve replacement surgery, damaged leaflets of the valve are excised and the annulus is sculpted to receive a replacement valve. Another less drastic method for treating defective valves is repair or reconstruction by annuloplasty, in which the valve annulus is re-shaped and held in place by attaching a prosthetic annuloplasty repair segment or ring to an interior wall of the heart around the valve annulus. The annuloplasty ring is designed to support the functional changes that occur during the cardiac cycle; maintaining coaptation and valve integrity.

One type of valvular insufficiency is ischemic mitral regurgitation (IMR). In IMR, the coordination of the mitral leaflets, the mitral annulus, the subvalvular apparatus and the left ventricular wall is upset in some way. There are many causes, such as congenital defects, rheumatic fever, endocarditis, etc. There is a classification system for IMR, which was developed by Carpentier. IMR is classified as either Type I, II, IIIa or IIIb, based mainly on leaflet motion.

The effects of valvular dysfunction vary, with IMR typically having more severe physiological consequences to the patient than tricuspid valve regurgitation. In either area of the heart, however, many of the defects are associated with dilation of the valve annulus. This dilation not only prevents competence of the valve but also results in distortion of the normal shape of the valve orifice. Remodeling of the annulus is therefore central to most reconstructive procedures on the valves. Clinical experience has shown that repair of the valves, when technically possible, produces better long-term results than valve replacement.

With regard to the mitral valve, many procedures have been described to correct the pathology of the valve leaflets and their associated chordae tendinae and papillary muscles. The mitral valve, in particular, is a bicuspid valve having a posterior leaflet that has an annulus insertion length that is larger than that of an anterior leaflet, which coapts or meets with the posterior leaflet. The part of the mitral valve annulus that is attached to the anterior leaflet is called the anterior aspect, while the part attached to the posterior leaflet is called the posterior aspect. The two leaflets are fused at two commissures that are inserted in the annulus just below the level of two cardiac trigones, called the anterolateral trigone and the posterolateral trigone.

In mitral valve repair, coaptation of the posterior and anterior leaflets is important. Also, it is considered important to preserve the normal distance between the two trigones. A significant surgical diminution of the inter-trigonal distance may cause left ventricular outflow obstruction and/or distortion of the base of the aortic valve. Thus, it is desirable to maintain the natural inter-trigonal distance and shape following mitral valve repair surgery.

Mitral valve annulus dilation tends to be confined to the posterior aspect, resulting in a posterior aspect that is larger than normal. Consequently, the repair of mitral valve annulus dilation generally involves reducing the size of the posterior aspect.

In the repair of mitral valve annulus dilation, the associated procedure begins with identification of the trigones. The distance between the trigones (i.e., inter-trigonal distance) remains practically constant during the cardiac cycle in any one particular patient, but may vary from 24 to 40 mm in length in patients. Annuloplasty devices used to treat mitral valve dilation are available in different sizes based upon the distance between the trigones along the anterior aspect (i.e., the aortic curtain). Alternatively, anterior and posterior commissures of the heart are used to size a valve annulus. Either way, it is critical to the successful outcome of the annuloplasty procedure to accurately determine the size of the annulus. Generally, the annuloplasty devices are available in even 2 mm increments from about 24 mm to about 40 mm.

Annuloplasty devices for mitral valve repair have generally been configured to restore the original, healthy shape of the mitral annulus at the end of systole. The ring is typically semi-rigid, planar and restores the primary anterior-posterior (A-P) dimension or ratio of the mitral valve annulus. The ring typically allows for sufficient coaptation of the leaflets at the end of systole.

For a given size of valve annulus, there may be a plurality of possible types of annuloplasty devices that may be implanted. The choice of device will depend upon the disease state or physiological problem associated with the valve. For example, with Barlow's disease, excess mitral valve leaflet tissue exists, which causes the mitral valve to leak back into the left atrium. Thus, with Barlow's disease, for example, an annuloplasty device having a design that accommodates excess leaflet tissue is desired. For example, a device having a longer anterior dimension, i.e., a larger A-P ratio, than standard devices may be used.

Annuloplasty device holders are used for holding annuloplasty devices during implantation. Such holders are used for positioning, holding, supporting and presenting the annuloplasty device during surgery. For mitral valve repair, the holders are typically a D-shaped body to which the annuloplasty device is sutured.

There is a continued desire to be able to improve annuloplasty devices to accommodate different physical structures of the heart due to different disease states of the heart. In addition, there is also a need for holders for such devices.

SUMMARY OF THE INVENTION

The present invention generally involves an adjustable annuloplasty device holder possible of having a plurality of different anterior-posterior (A-P) ratios. The holder can accommodate annuloplasty devices having a plurality of different anterior-posterior ratios, but pertaining to the same size (i.e., inter-trigonal or inter-commissural distances) of annulus.

Embodiments of the present invention offer advantages. The holder device of the present invention provides one holder device that is able to hold annuloplasty devices having different A-P ratios, but corresponding to the same size of valve annulus. Thus, an advantage of the present invention is that only one holder device needs to be made to accommodate a plurality of different annuloplasty devices. This reduces the cost and time associated with tooling holder devices for each separate annuloplasty device of a given inter-trigonal (or inter-commissural) distance and A-P ratio.

One aspect of the present invention is an adjustable annuloplasty device holder possible of having a plurality of different anterior-posterior ratios. The holder may comprise a member having an anterior segment and a posterior segment that are shaped to hold an anterior portion and a posterior portion, respectively, of an annuloplasty device, wherein the anterior segment has a given size and the posterior segment is adjustable in order to change the anterior-posterior ratio of the holder to accommodate annuloplasty devices having a plurality of different anterior-posterior ratios. The holder may further comprise a plurality of radially extending flanges in the posterior segment that are extendible varying distances in order to change the anterior-posterior ratio of the holder. The holder may also further comprise at least one detachable flange that may be attached to or detached from the member in order to change the anterior-posterior ratio of the holder. The member may have an outer circumferential surface to which at least the anterior portion of the annuloplasty device is mounted and the plurality of radially extending flanges may be slidably disposed within the member. The posterior portion of the annuloplasty device may be mounted to the plurality of flanges. The at least one detachable flange may be attached to the member by a snap-fit connection. The holder may comprise first and second detachable flanges, and the first detachable flange may be attached to the member and the second detachable flange may be attached to the first detachable flange. The first and second detachable flanges may be attached to the member and each other using snap-fit connections. The given size of the anterior segment may correspond to an inter-trigonal or inter-commissural distance of a heart valve annulus.

A second aspect of the present invention is a method of using an adjustable annuloplasty holder device. The method may comprise the steps of: receiving an adjustable annuloplasty device holder possible of having a plurality of different anterior-posterior ratios, the holder comprising a member having an anterior segment and a posterior segment that are shaped to hold an anterior portion and a posterior portion, respectively, of an annuloplasty device, wherein the anterior segment has a given size and the posterior segment is adjustable in order to change the anterior-posterior ratio of the holder to accommodate annuloplasty devices having a plurality of different anterior-posterior ratios; receiving an annuloplasty device of the given size of the anterior segment of the holder and of a given anterior-posterior ratio; adjusting the posterior segment of the holder such that the member has the given anterior-posterior ratio of the annuloplasty device; and mounting the annuloplasty device to the holder. The method may further comprise the steps of: delivering the annuloplasty device mounted on the holder to a heart valve annulus; suturing the annuloplasty device to the heart valve annulus; removing the annuloplasty device from the holder; and withdrawing the holder. The adjustable annuloplasty device holder may further comprise a plurality of radially extending flanges in the posterior segment that are extendible varying distances in order to change the anterior-posterior ratio of the holder, and the adjusting step may comprise extending the flanges to provide the given anterior-posterior ratio. The plurality of radially extending flanges may be slidably disposed within the member. The mounting step may comprise mounting the annuloplasty device to the plurality of flanges. The adjustable annuloplasty device holder may further comprise at least one detachable flange that may be attached to or detached from the member in order to change the anterior-posterior ratio of the holder, and the adjusting step may comprise attaching or detaching the at least one flange. The at least one detachable flange may be attached to the member by a snap-fit connection. The holder may comprise first and second detachable flanges, and the first detachable flange may be attached to the member and the second detachable flange may be attached to the first detachable flange. The first and second detachable flanges may be attached to the member and each other using snap-fit connections.

BRIEF DESCRIPTION OF THE DRAWINGS

The present invention will be further explained with reference to the appended Figures, wherein.

DETAILED DESCRIPTION OF PREFERRED EMBODIMENTS

With reference to the accompanying figures, wherein like components are labeled with like numerals throughout the several figures, an annuloplasty device holder is disclosed, taught and suggested.

In particular, the holder device of the present invention will correspond to one of a plurality of possible sizes of annulus, i.e., inter-trigonal or inter-commissural distances. The holder device will also be capable of holding annuloplasty devices that have different A-P ratios. A purpose of the holder device being able to hold annuloplasty device having varying A-P ratios is to reduce the number of holder devices that are necessary for a given set of annuloplasty devices.

Heart valve annuli having the same inter-trigonal (or inter-commissural) distance may have different A-P ratios due to different disease states of the valves, for example. Thus, a surgeon may measure the inter-trigonal distance (or inter-commissural distance) and may still have to choose between a plurality of annuloplasty devices having the corresponding size but having different A-P ratios. Having one device that can hold annuloplasty devices of the same size but different A-P ratios is more efficient to use. Preferably, the surgeon has a set of devices with different A-P ratios, and possibly different designs, available for each inter-trigonal (or inter-commissural) distance, or size, of annulus. The surgeon may then choose the appropriate device from the set in order to address the particular concerns with the annulus. Advantageously, the present invention provides the surgeon the ability to more specifically address a problem with a particular valve annulus.

For each size, or inter-trigonal (or inter-commissural) distance, of an annulus there are preferably a plurality of devices having varying A-P ratios that may be implanted. The plurality of devices with varying A-P ratios preferably correspond to different types or categories of annuloplasty devices. For instance, the A-P ratios may correspond to three different categories of devices that are designed to address different problems, pathologies, disease states, etc., relating to the heart. One category is preferably a remodeling (restorative) category that has a traditional annuloplasty device design, which reshapes the annulus that generally has a dilated posterior annulus. The remodeling (restorative) category of devices is preferably designed to address degenerative heart disease, myxomatous degeneration, fibroelastic deficiency, types I and II IMR, and degenerative diseases which result in a dilated posterior annulus, for examples. Another category is a restrictive category of devices, which is preferably designed to address cardiac ischemia, dilated cardiomyopathy, tethered leaflets in secondary mitral valve insufficiency, and Type IIIb IMR, for examples. And, a third category is an enlarging category of devices that is preferably designed to address Barlow's syndrome, systolic anterior motion (SAM) in Myxoid Heart Disease, septal hypertrophy, and Type II IMR, for examples. It is contemplated, however, that the set of devices may include additional types of devices that address additional or alternative heart conditions.

The present invention is described herein with regard to the treating the mitral valve of the heart. However, it is contemplated that the present invention may also apply to other valves of the heart (e.g., the tricuspid valve). Therefore, the categories and types of annuloplasty devices that the present invention may hold may also be different than those specifically described herein.

Figure 1:
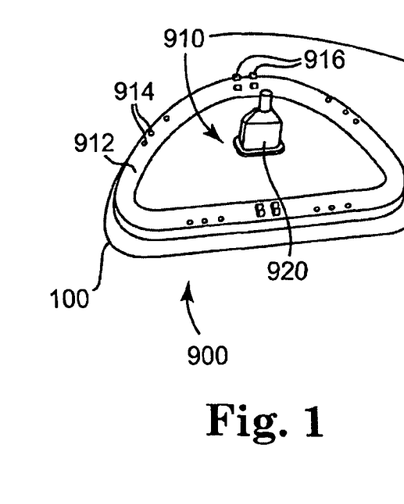
FIGS. 1-3 include perspective views of an embodiment of a holder of the present invention, shown in three configurations and holding three different annuloplasty devices having three different A-P ratios.
Figure 2:
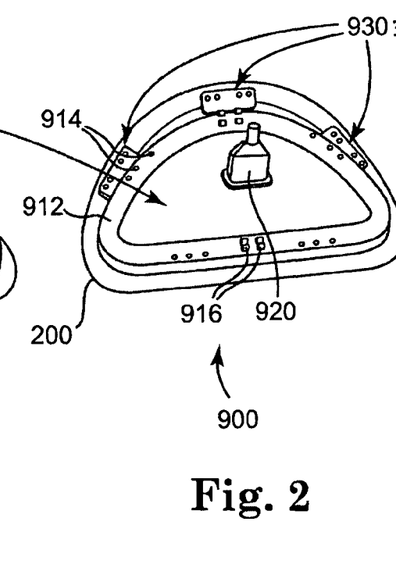
Figure 3:
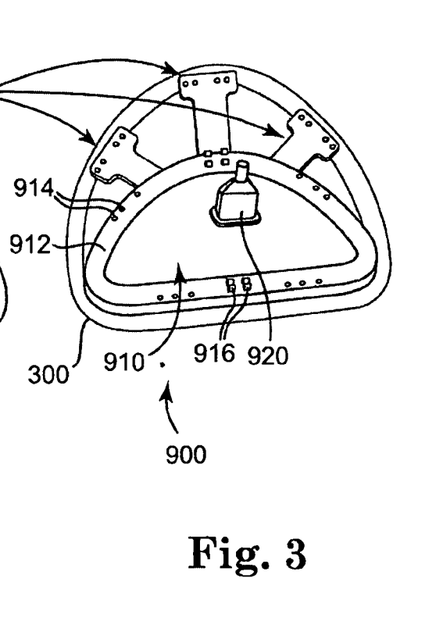

One embodiment of the present invention is shown in FIGS. 1-3. Holder device 900 is shown in three different configurations, in FIGS. 1-3, and is also shown holding one of three different annuloplasty devices 100, 200, 300, respectively, while in the three different configurations. The three annuloplasty devices 100, 200, 300 have the same inter-trigonal (or inter-commissural) distance, or size. The three configurations of the holder device 900 shown in FIGS. 1-3, however, each have a different anterior-posterior (A-P) ratio. The anterior dimension of the holder 900 (and A-P ratio) is increased from FIG. 1 to FIG. 2 and again from FIG. 2 to FIG. 3.

Holder device 900 comprises a plate 910 that is generally D-shaped. However, the sizing plate 910 may have any of a plurality of possible two-dimensional (2D) and three-dimensional (3D) shapes. The shape of the plate 910 depends upon the shape of a corresponding annuloplasty device. For example, the plate 910 may be planar or saddle-shaped.

The plate 910 preferably has an outer rim 912. The outer rim 912 preferably includes a plurality of suture holes 914 arranged around the outer rim 912, which are used to suture an annuloplasty device to the plate 910. Additionally, the plate 910 preferably includes suture holders for cutting 916. The suture holders for cutting 916 are preferably configured such that a suture may pass or be threaded between the holders 916, and such that a scalpel can fit through or between the suture holders 916 in order to cut the suture. A scalpel may be used to cut the suture or sutures that is threaded through the suture holders 916, in order to release the annuloplasty, or other, device from the holder plate 910.

Although not shown in the figures, the plate 910 may also include markings. Some exemplary markings include, but are not limited to the product name, size and CE mark.

The plate 910 preferably has an outer circumference equal to the inner circumference of at least one annuloplasty device with which it is used. As shown in FIG. 1, the plate 910 is shaped and sized to correspond to annuloplasty device 100. The annuloplasty device 100 is preferably sutured to the plate 910.

The plate 910 is preferably made from biocompatible material that is also preferably optically transparent and rigid to the degree that it maintains a shape. The material could have a degree of deformability to minimize tissue trauma while introducing the holder through the surgical incision site. An exemplary material for the holder device is polysulfone or another similar thermoplastic. Some other exemplary materials, however, include stainless steel, polyacetal resin, titanium, rubber, etc. Other materials are also contemplated.

The thickness of the plate 910 is preferably minimized while still retaining substantial strength to prevent substantial flexing or bending or to prevent breakage. The thickness is minimized in order to prevent optical distortion through the plate 910 and/or in order to allow the sizing plate 910 to fit through relatively small openings, such as an annulus.

The plate 910 is shown having a continuous surface. However, the plate 910 may alternatively be discontinuous and may include voids. An exemplary use of such a void may be to thread a suture or other lanyard through the void in order to tether the plate 910 should it come loose from a handle while in a patient's body.

An attachment hub 920 is preferably located on one of two major surfaces of plate 910. The purpose of the attachment hub 920 is to provide a location for an elongate member (not shown) to be connected or attached to the holder device 900. Such an elongate member may be used to deliver the holder device 900 to a desired surgical site, and also for removal of the holder device 900 from the surgical site once the annuloplasty device has been removed from the holder 900.

The device 900 of FIG. 1 may also be modified in order to hold devices having larger A-P ratios than that of device 100. For instance, device 200 in FIG. 2 has a larger A-P ratio, and is shown being held on device 900 in the configuration shown. The inter-trigonal distance of the device 900 stays the same, as can be seen by comparing device 900 in FIGS. 1 and 2. However, the anterior dimension is increased, which similarly increases the A-P ratio of the device 900.

In order for holder device 900 to accommodate a device, such as device 200, having a larger A-P ratio, a plurality of radially extending flanges 930 are extended from the plate 910 in order to engage a posterior portion of the device 200. The plurality of radially extending flanges 930 are slidably disposed in channels or slots (not shown) in plate 910. Preferably, as shown, there are three radially extending flanges 930, however other numbers are also contemplated by the present invention.

Flanges 930 are preferably injection molded components that mate with a slot or channel in holding plate 910. The flanges 930 are preferably snap fit into the slots, however other means for removably attaching the flanges 930 are also contemplated by the present invention. Some other exemplary means for attachment include sonic welding, laser welding, adhesives and magnetics, for example.

FIG. 3 shows the radially extending flanges 930 extended even further than in FIG. 2. The flanges 930 are then able to accommodate a posterior portion of device 300, which has a larger A-P ratio than that of devices 100 and 200. The flanges 930 may include suture holes in order to secure the flanges 930 to an annuloplasty device, for example.

Holder device 900 is only shown in three different A-P ratios in FIGS. 1-3. However, it is contemplated that the device 900 may be capable of having a different number of and different A-P ratios than those shown. Holder device 900 shown is merely representative of many different contemplated sizes and shapes/types of holder devices that may be configured as in FIGS. 1-3.

An advantage of holder device 900 is that the plate 910, for all the possible A-P ratios of a size of annuloplasty device, is the same. Therefore, the plate 910 may be easily injection-molded.

Holder device 900 is preferably used to deliver an annuloplasty device (e.g., devices 100, 200, and 300) for implantation. The annuloplasty device would be attached to the holder device 900, which would be preferably connected to an elongate handle (not shown) at attachment member 920. The holder device 900 would then be delivered to a desired valve annulus in a body. Next, the annuloplasty device would then be sutured to the annulus and removed from the holder device 900. The holder device 900 would then be retracted from the body.

Figure 4:
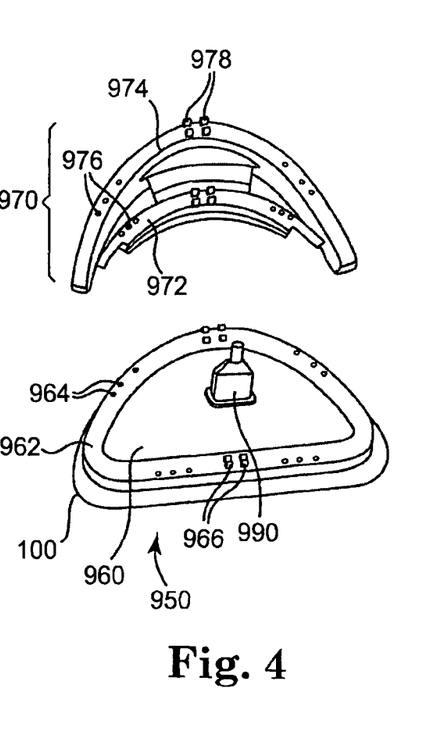
FIGS. 4-6 include perspective views of another embodiment of a holder of the present invention shown in three configurations and holding three different annuloplasty devices having three different A-P ratios.
Figure 5:
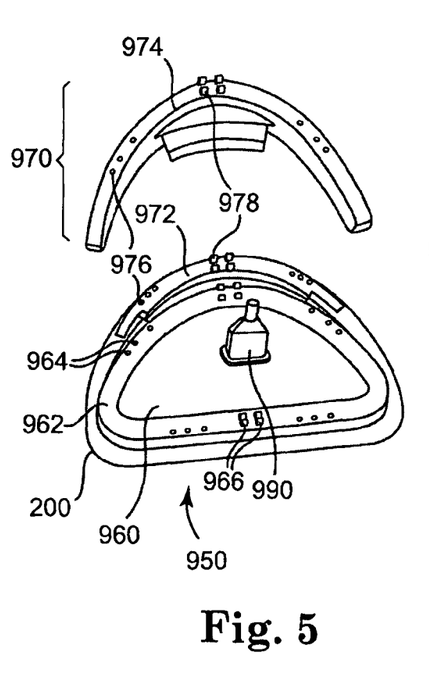
Figure 6:
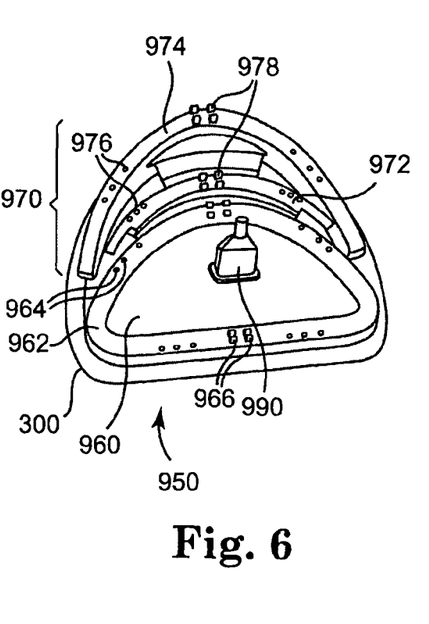

A second embodiment of a holder device of the present invention is shown in FIGS. 4-6. In FIG. 4, holder device 950 is shown comprising a plate 960 and a detachable flange 970 that is comprised of first and second parts 972, 974, respectively. FIG. 4 shows an annuloplasty device 100 attached to the plate 960 of holder device 950. Neither first part 972 nor second part 974 of the detachable flange 970 is attached to plate 960 because the A-P ratio of the plate 960 generally matches the A-P ratio of annuloplasty device 100.

In order for holder device 950 to hold an annuloplasty device having the same inter-trigonal distance as device 100 but having a larger A-P ratio (e.g., devices 200 and 300), the first part 972 and possibly the second part 974 of the detachable flange 970 are attached to plate 960. FIG. 5 shows the first part 972 of the flange 970 attached to plate 960, which increased the A-P ratio of the holder device 950. Device 200 is shown being held on the holder device 950 in FIG. 5. FIG. 6 shows the second part 974 of the flange 970 also attached to the first part 972 and the plate 960, which increased the A-P ratio of the device 950 from that shown in FIG. 5. Device 300 is shown attached to the holder device 950 of FIG. 6.

First 972 and second 974 parts of detachable flange 970 are preferably attached to each other and plate 960 by snap fit. However, other means for releasable attachment are also contemplated, such as sonic welding, laser welding, adhesives and magnetics, for example.

The plate 960 preferably includes an outer rim 962. The outer rim 962 preferably includes suture holes 964, as shown. The location and number of the suture holes 964 shown, however, is exemplary, and other locations and numbers are contemplated. Suture holes 976 are also found on the detachable flange 970.

The outer rim 962 also preferably includes suture holders for cutting 966. The suture holders for cutting 966 are preferably configured such that a suture may pass or be threaded between the holders 966, and such that a scalpel can fit through or between the suture holders 966 in order to cut the suture. A scalpel may be used to cut the suture or sutures that is threaded through the suture holders 966, in order to release the annuloplasty, or other, device from the plate 960.

Although not shown in the figures, the plate 960 may also include markings. Some exemplary markings include, but are not limited to the product name, size and CE mark.

The first 972 and second 974 parts of the detachable flange 970 are generally semi-circular in shape. The first and second parts 972, 974 are reversibly attachable and detachable to/from the plate 960 on the posterior portion and to each other.

First 972 and second 974 parts of flange 970 also include suture holes 976 and suture holders for cutting 978. The suture holders for cutting 978 are preferably configured such that a suture may pass or be threaded between the holders, and such that a scalpel can fit through or between the suture holders 978 in order to cut the suture. A scalpel may be used to cut the suture or sutures that is threaded through the suture holders 978, in order to release the annuloplasty, or other, device from the plate 960 and flange 970.

Other designs of the flange parts 972, 974 are also contemplated by the present invention. The other designs may be attached and removed from the plate 960 in order to allow the holder device 950 to have different A-P ratios.

The plate 960 may comprise similar materials to plate 910 of device 900 described above. Additionally, the first 972 and second parts 974 of the flange 970 may be made of similar materials as well.

As with the embodiment shown in FIGS. 1-3, only three A-P ratios are represented in holder device 950. However, it is contemplated that additional and different A-P ratios may be possible using device 950. The device 950 shown is merely representative of many different contemplated sizes and shapes/types of holder devices that may be configured in accordance with the embodiment of FIGS. 4-6.

Holder device 950 is preferably used to deliver an annuloplasty device (e.g., devices 100, 200, 300) for implantation. The annuloplasty device would be attached to the holder device 950, which would be connected to an elongate handle (not shown) at an attachment member 990. The holder device 950 would then be delivered to a desired valve annulus in a body. Next, the annuloplasty device would then be sutured to the annulus and removed from the holder device 950. The holder device 950 would then be retracted from the body.

It is to be understood that while particular embodiments of the invention have been illustrated for use in typical valve repair procedures, various modifications to shape, and arrangement of parts can be made as may be desirable for varying applications as may relate to valve sizes or later developed techniques. The invention should not be considered limited to the specific methods and devices precisely described herein. On the contrary, various modifications will be apparent to those of ordinary skill upon reading the disclosure. Although certain embodiments are described with reference to the mitral valve, use with other valves or anatomical structures is also contemplated. The foregoing detailed description has been given for clarity of understanding only. No unnecessary limitations are to be understood.

The invention claimed is:

1. A method of using an adjustable annuloplasty holder device, the method comprising the steps of:

receiving an adjustable annuloplasty device holder possible of having a plurality of different anterior-posterior ratios as the inter-trigonal distance remains constant, the holder comprising a member having an anterior segment and a posterior segment that are shaped to hold an anterior portion and a posterior portion, respectively, of a first annuloplasty device having a first anterior-posterior ratio, wherein the anterior segment has a given size and the holder is adjustable by a component attachable to the member without changing the constant inter-trigonal distance in order to change the anterior-posterior ratio of the holder to accommodate annuloplasty devices having a plurality of different anterior-posterior ratios greater than the first anterior-posterior ratio, the member comprising an outer rim for holding the first annuloplasty device;

receiving an annuloplasty device of the given size of the anterior segment of the holder and of a given anterior-posterior ratio greater than the first anterior-posterior ratio;

adjusting the posterior segment of the holder such that the member has the given anterior-posterior ratio of the annuloplasty device; and mounting the annuloplasty device to the holder.

2. The method of claim 1, further comprising the steps of:

delivering the annuloplasty device mounted on the holder to a heart valve annulus;

suturing the annuloplasty device to the heart valve annulus;

removing the annuloplasty device from the holder; and withdrawing the holder.

3. The method of claim 1, wherein the component is one of a plurality of flanges extending radially from the posterior segment by varying distances in order to change the anterior-posterior ratio of the holder, and the adjusting step involves extending the flanges to provide the given anterior-posterior ratio.

4. The method of claim 3, wherein the plurality of radially extending flanges are slidably disposed within the member.

5. A method of using an adjustable annuloplasty holder device, the method comprising the steps of:

receiving an adjustable annuloplasty device holder possible of having a plurality of different anterior-posterior ratios as the inter-trigonal distance remains constant, the holder comprising a member having an anterior segment and a posterior segment that are shaped to hold an anterior portion and a posterior portion, respectively, of an annuloplasty device, wherein the anterior segment has a given size and the posterior segment is adjustable without changing the constant inter-trigonal distance in order to change the anterior-posterior ratio of the holder to accommodate annuloplasty devices having a plurality of different anterior-posterior ratios;

receiving an annuloplasty device of the given size of the anterior segment of the holder and of a given anterior-posterior ratio;

adjusting the posterior segment of the holder such that the member has the given anterior-posterior ratio of the annuloplasty device; and mounting the annuloplasty device to the holder;

wherein the adjustable annuloplasty device holder further comprises a plurality of radially extending flanges in the posterior segment that are extendible varying distances in order to change the anterior-posterior ratio of the holder, and the adjusting step involves extending the flanges to provide the given anterior-posterior ratio; and wherein the mounting step comprises mounting the annuloplasty device to the plurality of flanges.

6. A method of using an adjustable annuloplasty holder device, the method comprising the steps of:

receiving an adjustable annuloplasty device holder possible of having a plurality of different anterior-posterior ratios, the holder comprising a member having an anterior segment and a posterior segment that are shaped to hold an anterior portion and a posterior portion, respectively, of an annuloplasty device, wherein the anterior segment has a given size and the posterior segment is adjustable in order to change the anterior-posterior ratio of the holder to accommodate annuloplasty devices having a plurality of different anterior-posterior ratios;

receiving an annuloplasty device of the given size of the anterior segment of the holder and of a given anterior-posterior ratio;

adjusting the posterior segment of the holder such that the member has the given anterior-posterior ratio of the annuloplasty device; and mounting the annuloplasty device to the holder, wherein the adjustable annuloplasty device holder further comprises at least one detachable flange that is attachable to or detachable from the member in order to change the anterior-posterior ratio of the holder without changing the constant inter-trigonal distance, and the adjusting step comprises attaching or detaching the at least one flange.

7. The method of claim 6, wherein the at least one detachable flange is attachable to the member by a snap-fit connection.

8. The method of claim 6, wherein the holder comprises first and second detachable flanges, and the first detachable flange is attachable to the member and the second detachable flange is attachable to the first detachable flange.

9. The method of claim 8, wherein the first and second detachable flanges are attachable to the member and each other using snap-fit connections.

* * * * *